(12) United States Patent
Parthasaradhi Reddy et al.

(10) Patent No.: US 8,598,341 B2
(45) Date of Patent: Dec. 3, 2013

(54) PROCESS FOR ETRAVIRINE INTERMEDIATE AND POLYMORPHS OF ETRAVIRINE

(75) Inventors: Bandi Parthasaradhi Reddy, Andhra Pradesh (IN); Kura Rathnakar Reddy, Andhra Pradesh (IN); Dasari Muralidhara Reddy, Andhra Pradesh (IN); Rapolu Raji Reddy, Andhra Pradesh (IN); Bandi Vamsi Krishna, Andhra Pradesh (IN); Adulla Venkat Narsimha Reddy, Andhra Pradesh (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 13/805,920

(22) PCT Filed: Jun. 28, 2010

(86) PCT No.: PCT/IN2010/000442
§ 371 (c)(1),
(2), (4) Date: Dec. 20, 2012

(87) PCT Pub. No.: WO2012/001695
PCT Pub. Date: Jan. 5, 2012

(65) Prior Publication Data
US 2013/0096148 A1 Apr. 18, 2013

(51) Int. Cl.
*C07D 239/00* (2006.01)
(52) U.S. Cl.
USPC .......................................................... 544/242

(58) Field of Classification Search
None
See application file for complete search history.

(56) References Cited

U.S. PATENT DOCUMENTS

| | | | |
|---|---|---|---|
| 7,037,917 B2 | 5/2006 | De Corte et al. | |
| 2006/0106043 A1 | 5/2006 | Kraft et al. | |
| 2009/0105147 A1 | 4/2009 | Masse | |
| 2013/0035485 A1* | 2/2013 | Krizmanic et al. | 544/316 |

OTHER PUBLICATIONS

Joshi et al.; "An Improved Synthesis of Etravirine"; Organic Process Research & Development; 14; pp. 667-660; (2010).
International Search Report; International Application No. PCT/IN2010/000442; International Filing Date Jun. 28, 2010; Date of Mailing Apr. 18, 2011; 6 pages.

* cited by examiner

*Primary Examiner* — James O Wilson
*Assistant Examiner* — Oluwafemi Masha
(74) *Attorney, Agent, or Firm* — Cantor Colburn LLP

(57) ABSTRACT

4-[[6-chloro-2-[(4-cyanophenyl)amino]-4-pyrimidinyl]oxy]-3,5-dimethyl-benzonitrile is a key intermediate for the preparation of etravirine. The present invention provides a process for preparation of 4-[[6-chloro-2-[(4-cyanophenyl)amino]-4-pyrimidinyl]oxy]-3,5-dimethylbenzonitrile. The present invention also provides a novel process for the preparation of etravirine crystalline form I. The present invention further provides novel crystalline forms of etravirine, processes for their preparation and pharmaceutical compositions comprising them.

23 Claims, 3 Drawing Sheets

US 8,598,341 B2

PROCESS FOR ETRAVIRINE INTERMEDIATE AND POLYMORPHS OF ETRAVIRINE

CROSS-REFERENCE TO RELATED APPLICATIONS

This application is a 371 of PCT/IN2010/000442 filed Jun. 28, 2010, under the provisions of 35 U.S.C. 119 and the International Convention for the protection of Industrial Property, which is incorporated herein by reference.

FIELD OF THE INVENTION

4-[[6-chloro-2-[(4-cyanophenyl)amino]-4-pyrimidinyl]oxy]-3,5-dimethyl-benzonitrile is a key intermediate for the preparation of etravirine. The present invention provides a process for preparation of 4-[[6-chloro-2-[(4-cyanophenyl)amino]-4-pyrimidinyl]oxy]-3,5-dimethylbenzonitrile. The present invention also provides a novel process for the preparation of etravirine crystalline form I. The present invention further provides novel crystalline forms of etravirine, processes for their preparation and pharmaceutical compositions comprising them.

BACKGROUND OF THE INVENTION

Etravirine is chemically, 4-[[4-amino-5-bromo-6-(4-cyano-2,6-dimethylphenyloxy)-2-pyrimidinyl]amino]benzonitrile and has the structural formula:

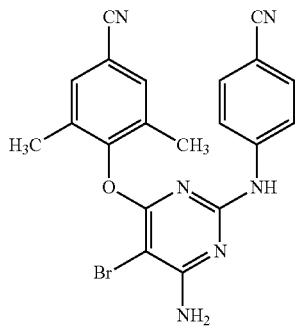 [SMILES: Cc1cc(C#N)cc(C)c1Oc1nc(Nc2ccc(C#N)cc2)nc(N)c1Br]

Etravirine is a drug used for the treatment of HIV. Etravirine is a non-nucleoside reverse transcriptase inhibitor (NNRTIs). Unlike the currently available agents in the class, resistance to other NNRTIs does not seem to confer resistance to etravirine. Etravirine is marketed under the brand name Intelence® by Tibotec.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning Calorimetry (DSC) and Infrared spectrometry (IR).

Solvent medium and mode of crystallization play very important role in obtaining a crystalline form over the other.

Etravirine can exist in different polymorphic forms, which differ from each other in terms of stability, physical properties, spectral data and methods of preparation.

Etravirine and its salts were described in U.S. Pat. No. 7,037,917. According to the patent also described a process for the preparation of etravirine which comprises treating 4-[[6-chloro-5-bromo-2[(4-cyanophenyl)amino]-4-pyrimidinyl]oxy]-3,5-dimethylbenzonitrile with ammonia.

Process for the preparation of etravirine was described in *Drugs of the Future* 2005, 30(5): 462-468. According to the process of etravirine which comprises treating 4-[[6-chloro-5-bromo-2[(4-cyanophenyl)amino]-4-pyrimidinyl]oxy]-3,5-dimethylbenzo-nitrile with ammonia.

Process for the preparation of 4-[[6-chloro-2-[(4-cyanophenyl)amino]-4-pyrimidinyl]oxy]-3,5-dimethylbenzonitrile was described in *Organic process research & development.*, 2010, 14(3); 657-660. According to the process of 4-[[6-chloro-2-[(4-cyanophenyl)amino]-4-pyrimidinyl]oxy]-3,5-dimethylbenzonitrile which comprises reacting 4-aminobenzonitrile in N-methylpyrrolidone with 4-[(2,6-dichloro)-4-pyrimidinyloxy]-3,5-dimethylbenzonitrile in the presence of potassium tert-butoxide.

Process for the preparation of etravirine was described in *Organic process research & development.*, 2010, 14(3); 657-660. According to the publication, crystalline solid of etravirine was obtained by dissolving crude etravirine in acetone at 50 to 55° C. and was treated with activated charcoal, and isolating. The crystalline etravirine obtained by the process of the prior art is herein after designated as etravirine crystalline form I. The powdered x-ray diffractogram (PXRD) of etravirine crystalline Form I is shown in FIG. 1. Crystalline Form I is characterized by peaks in the powder x-ray diffraction spectrum having 2θ angle positions at about 8.7, 9.1, 13.0, 19.4, 19.6, 23.5, 26.5, 26.8 and 28.5±0.2 degrees.

We have discovered novel process for the preparation of 4-[[6-chloro-2-[(4-cyanophenyl)amino]-4-pyrimidinyl]oxy]-3,5-dimethylbenzonitrile. 4-[[6-chloro-2-[(4-cyanophenyl)amino]-4-pyrimidinyl]oxy]-3,5-dimethylbenzonitrile is a key intermediate for the preparation of etravirine.

We have also discovered a process for the preparation of consistently reproducible etravirine crystalline form I.

We have also discovered that etravirine can be prepared in two well-defined and consistently reproducible crystalline forms.

Thus, one object of the present invention is to provide a process for the preparation of 4-[[6-chloro-2-[(4-cyanophenyl)amino]-4-pyrimidinyl]oxy]-3,5-dimethylbenzonitrile.

Another object of the present invention is to provide a process for the preparation of etravirine crystalline form I.

Yet another object of the present invention is to provide novel crystalline forms of etravirine, process for their preparation and pharmaceutical compositions comprising them.

SUMMARY OF THE INVENTION

In one aspect, the present invention provided a novel process for the preparation of 4-[[6-chloro-2-[(4-cyanophenyl)amino]-4-pyrimidinyl]oxy]-3,5-dimethylbenzonitrile of formula I:

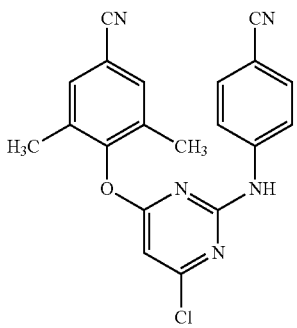

which comprises reacting the 4-(4,6-dichloropyrimidine-2-yl-amino)benzonitrile of formula II:

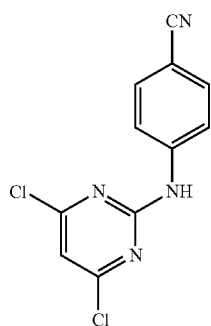

with 4-hydroxy-3,5-dimethylbenzonitrile of formula III:

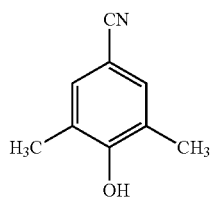

in the presence of a base to obtain a compound of formula I.

In another aspect, the present invention provided a process for the preparation of etravirine crystalline form I, which comprises:
 a) providing a solution of etravirine in an organic solvent;
 b) adding a solvent selected from water and hydrocarbon solvent to the solution obtained in step (a); and
 c) isolating etravirine crystalline from I.

In another aspect, the present invention provided a crystalline form of etravirine designated as form II characterized by peaks in the powder x-ray diffraction spectrum having 2θ angle positions at about 11.1, 12.2, 13.1, 13.8, 18.1, 18.4, 19.8, 21.3, 22.7, 22.9, 24.5 and 27.2±0.2 degrees.

In another aspect, the present invention provided a process for the preparation of etravirine crystalline form II, which comprises:
 a) providing a solution of etravirine in a mixture of alcoholic solvent and chlorinated solvent in a ratio of 0.7:1 to 1.2:1;
 b) removing the solvent completely from the solution obtained in step (a); and
 c) drying the solid obtained in step (b) to obtain etravirine crystalline from II.

In another aspect, the present invention provided a crystalline form of etravirine designated as form III characterized by peaks in the powder x-ray diffraction spectrum having 2θ angle positions at about 6.0, 8.7, 9.1, 11.2, 12.1, 13.7, 18.1, 19.8, 22.9, 24.4, 25.3 and 27.3±0.2 degrees.

In another aspect, the present invention provided a process for the preparation of etravirine crystalline form III, which comprises:
 a) stirring a solution of etravirine in a mixture of alcoholic solvent and chlorinated solvent in a ratio of 1.3:1 to 2:1;
 b) removing the solvent partially or completely from the solution obtained in step (a);
 c) adding ether solvent to the reaction mass obtained in step (b); and
 d) isolating etravirine crystalline from 3.

In yet another aspect, the present invention provided a pharmaceutical composition comprising crystalline forms of etravirine selected from crystalline form II and crystalline form III or a mixture thereof; and a pharmaceutically acceptable excipient.

Figure 1:
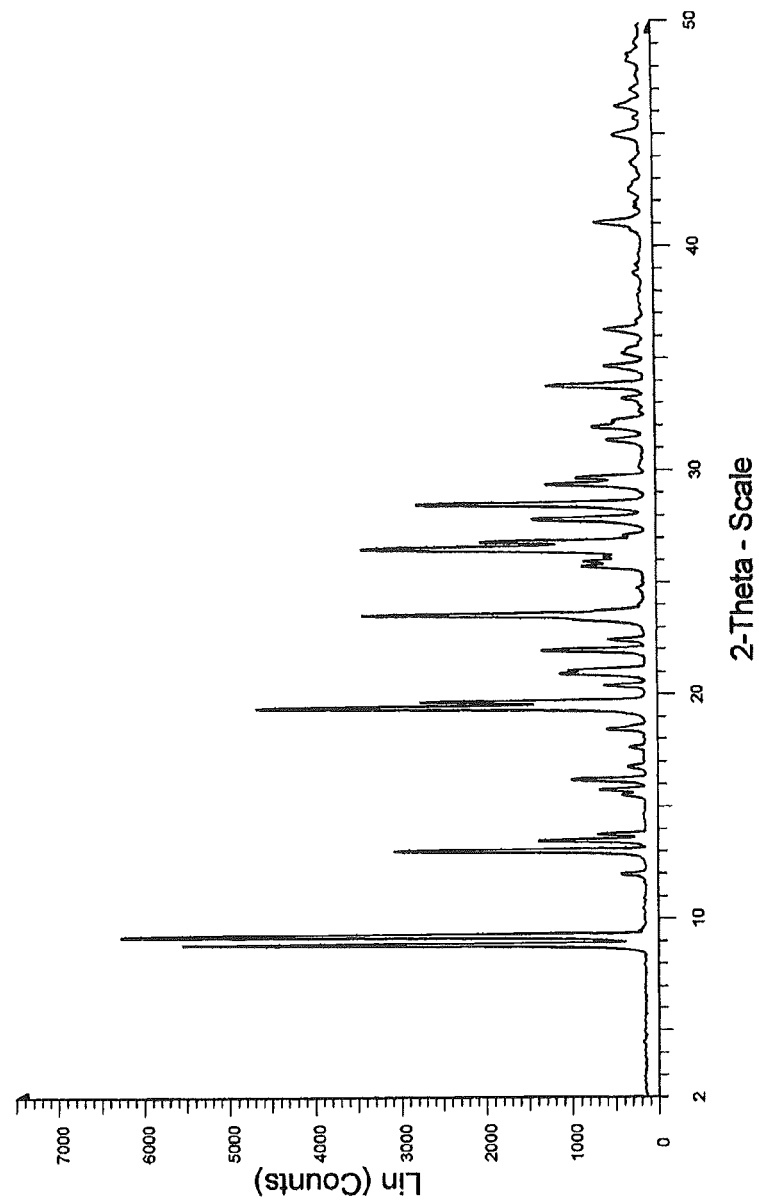
FIG. 1 is X-ray powder diffraction spectrum of etravirine crystalline form I.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.02 degrees to theta per step and a step of 10.4 seconds. The sample was simply placed on the sample holder. The sample was rotated at 30 rpm at a voltage 40 KV and current 35 mA.

DETAILED DESCRIPTION OF THE INVENTION

According to one aspect of the present, there is provided a novel process for the preparation of 4-[[6-chloro-2-[(4-cyanophenyl)amino]-4-pyrimidinyl]oxy]-3,5-dimethylbenzonitrile of formula I:

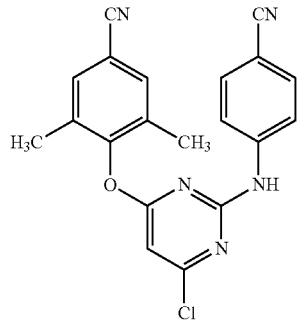

which comprises reacting the 4-(4,6-dichloropyrimidine-2-yl-amino)benzonitrile of formula II:

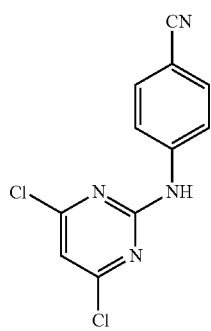

with 4-hydroxy-3,5-dimethylbenzonitrile of formula III:

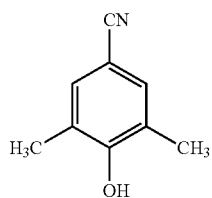

in the presence of a base to obtain a compound of formula I.

Preferably the base used in the process may be organic base or inorganic base and more preferable base is inorganic base selected from alkali metal hydroxides, alkali metal carbonates or alkali metal bicarbonates. Still more preferable base is potassium carbonate.

The reaction may preferably be carried out in a solvent selected from N-methylpyrrolidone, dimethylformamide, dimethylacetamide and dioxane, and more preferable solvent is N-methylpyrrolidone.

According to another aspect of the present invention, there is provided a process for the preparation of etravirine crystalline form I, which comprises:
a) providing a solution of etravirine in an organic solvent;
b) adding a solvent selected from water and hydrocarbon solvent to the solution obtained in step (a); and
c) isolating etravirine crystalline from I.

Etravirine used in step (a) may preferably be etravirine obtained by the known process or etravirine crystalline form II of the invention or etravirine crystalline form III of the invention.

The organic solvent used in step (a) may preferably be a solvent or mixture of solvents selected from the group consisting of an alcoholic solvents such as methanol, ethanol and isopropyl alcohol; an ester solvents such as ethyl acetate, methyl acetate, isopropyl acetate, tert-butyl methyl acetate and ethyl formate; acetonitrile; dimethylformamide; dimethylsulfoxide; an chlorinated solvents such as methylene chloride, chloroform, carbontetrachloride and ethylene dichloride; an ether solvents such as tetrahydrofuran, 1,4-dioxane, tert-butyl methyl ether and diethyl ether; N-methylpyrrolidone and dimethylacetamide. More preferable solvent is an ether solvent, N-methylpyrrolidone and dimethylacetamide, and still more preferable solvent is tetrahydrofuran, 1,4-dioxane, N-methylpyrrolidone and dimethylacetamide.

The hydrocarbon solvent used in step (b) may preferably be a solvent or mixture of solvents selected from cyclohexane, hexane, n-heptane, benzene, toluene and xylene, and more preferable hydrocarbon solvent is n-heptane.

The reaction in step (b) may optionally be carried out in the presence of etravirine crystalline form I crystals.

Isolation of etravirine crystalline form I in step (c) may preferably be performed by conventional techniques such as centrifugation and filtration.

Figure 2:
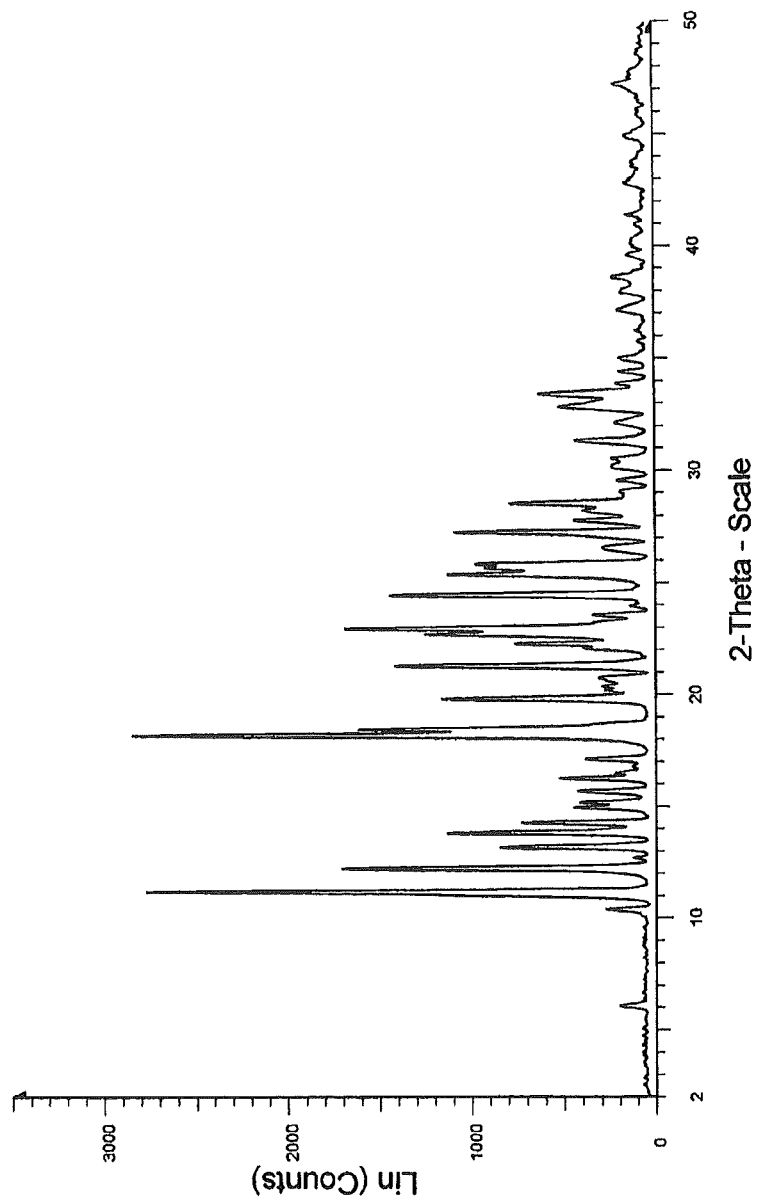
FIG. 2 is X-ray powder diffraction spectrum of etravirine crystalline form II.

According to another aspect of the present invention, there is provided a crystalline form of etravirine designated as form II characterized by peaks in the powder x-ray diffraction spectrum having 2θ angle positions at about 11.1, 12.2, 13.1, 13.8, 18.1, 18.4, 19.8, 21.3, 22.7, 22.9, 24.5 and 27.2±0.2 degrees. The powdered x-ray diffractogram (PXRD) of etravirine crystalline form II is shown in FIG. 2.

According to another aspect of the present invention, there is provided a process for the preparation of etravirine crystalline form II, which comprises:
a) providing a solution of etravirine in a mixture of alcoholic solvent and chlorinated solvent in a ratio of 0.7:1 to 1.2:1;
b) removing the solvent completely from the solution obtained in step (a); and
c) drying the solid obtained in step (b) to obtain etravirine crystalline from II.

Etravirine used in step (a) may preferably be etravirine obtained by the known process or etravirine crystalline form I or etravirine crystalline form III of the invention.

The alcoholic solvent used in step (a) may preferably be a solvent or mixture of solvents selected from methanol, ethanol and isopropyl alcohol, and more preferable alcoholic solvent is methanol.

The chlorinated solvent used in step (a) may preferably be a solvent or mixture of solvents selected from methylene chloride, chloroform, carbontetrachloride and ethylene dichloride, and more preferable chlorinated solvent is methylene dichloride.

Removal of the solvent in step (b) may be carried out at atmospheric pressure or at reduced pressure. Removal of the solvent may preferably be carried out until the solvent is almost completely distilled off.

The reaction in step (b) may optionally be carried out in the presence of etravirine crystalline form II crystals.

Drying of the solid in step (c) may be carried out at 45 to 55° C. under high vacuum.

Figure 3:
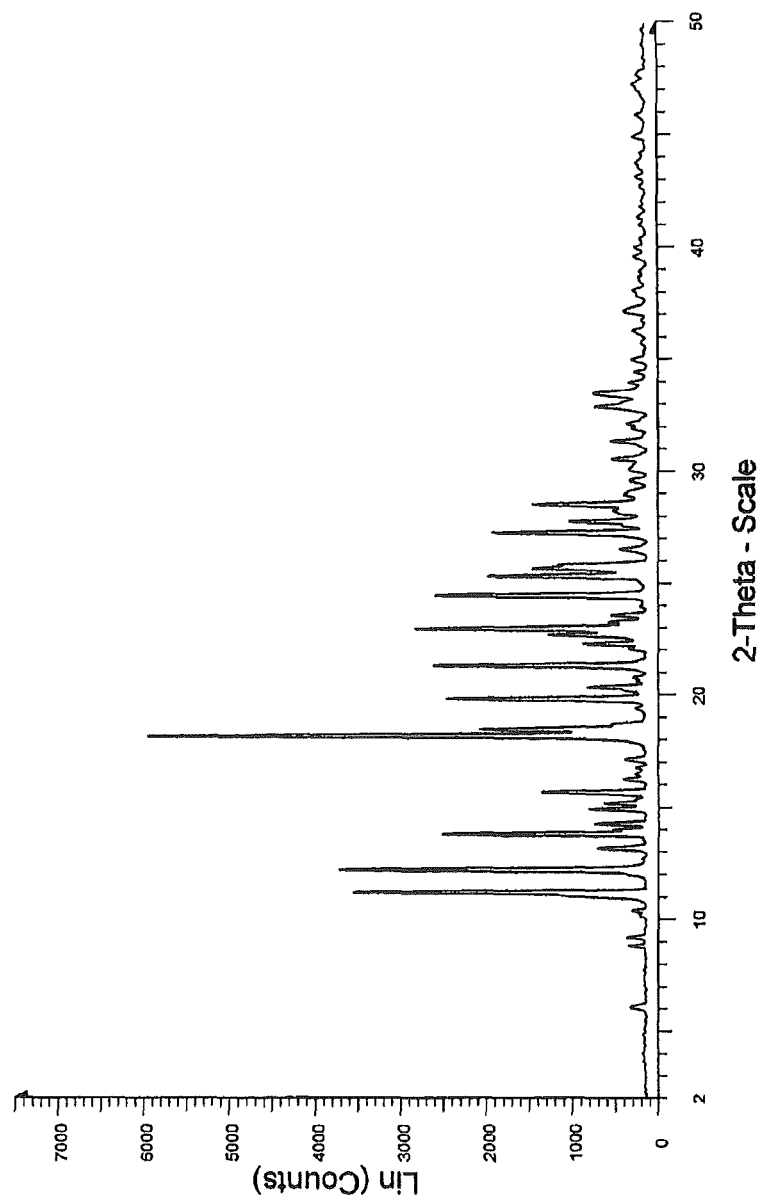
FIG. 3 is X-ray powder diffraction spectrum of etravirine crystalline form III.

According to another aspect of the present invention, there is provided a crystalline form of etravirine designated as form III characterized by peaks in the powder x-ray diffraction spectrum having 2θ angle positions at about 6.0, 8.7, 9.1, 11.2, 12.1, 13.7, 18.1, 19.8, 22.9, 24.4, 25.3 and 27.3±0.2 degrees. The powdered x-ray diffractogram (PXRD) of etravirine crystalline form III is shown in FIG. 3.

According to another aspect of the present invention, there is provided a process for the preparation of etravirine crystalline form III, which comprises:
a) stirring a solution of etravirine in a mixture of alcoholic solvent and chlorinated solvent in a ratio of 1.3:1 to 2:1;
b) removing the solvent partially or completely from the solution obtained in step (a);
c) adding ether solvent to the reaction mass obtained in step (b); and
d) isolating etravirine crystalline from III.

Etravirine used in step (a) may preferably be etravirine obtained by the known process or etravirine crystalline form I or etravirine crystalline form II of the invention.

The alcoholic solvent used in step (a) may preferably be a solvent or mixture of solvents selected from methanol, ethanol and isopropyl alcohol, and more preferable alcoholic solvent is methanol.

The chlorinated solvent used in step (a) may preferably be a solvent or mixture of solvents selected from methylene chloride, chloroform, carbontetrachloride and ethylene dichloride, and more preferable chlorinated solvent is methylene dichloride.

Removal of the solvent may be carried out in step (b) at atmospheric pressure or at reduced pressure. Removal of the solvent may preferably be carried out until the solvent is almost completely distilled off.

The ether solvent used in step (c) may preferably be a solvent or mixture of solvents selected from tetrahydrofuran, 1,4-dioxane, tert-butyl methyl ether and diethyl ether, and more preferably ether solvent is tert-butyl methyl ether.

The reaction in step (c) may optionally be carried out in the presence of etravirine crystalline form III crystals.

Isolation of etravirine crystalline form III in step (d) may preferably be performed by conventional techniques such as centrifugation and filtration.

According to another aspect of the present invention, there is provided a pharmaceutical composition comprising novel crystalline forms of etravirine selected from crystalline form II and crystalline form III or a mixture thereof; and a pharmaceutically acceptable excipient.

The pharmaceutically acceptable inert carrier which can be used may be a solid to or liquid.

The solid pharmaceutical preparation is in the form of tablets, capsules, powders and pills.

The liquid pharmaceutical preparation includes solutions, suspensions, syrups, elixirs and emulsions.

The invention will now be further described by the following examples, which are illustrative rather than limiting.

EXAMPLES

Preparation of 1-(4-cyanophenyl)guanidine

Preparative Example 1

A solution of P-aminobenzonitrile (100 gm), ethanol (500 ml), concentrated nitric acid (36 ml) and aqueous cyanamide (50%, 54 ml) was heated at reflux. The solution was maintained for 16 hours at reflux. The reaction mass was further cooled to 0° C. and then added methyl tert-butyl ether (500 ml) at 0 to 5° C. The reaction mass was maintained for 5 hours at 0 to 5° C. and separated solid obtained was collected by filtration to obtain 59 gm of guanidine nitrate.

Guanidine nitrate (59 gm) was dissolved in water (590 ml) and then added sodium hydroxide solution (1M, 325 ml). The separated solid obtained was filtered and dried to obtain 33 gm of 1-(4-cyanophenyl)guanidine.

Preparation of 4-(4,6-dihydroxypyrimidine-2-yl-amino)benzonitrile

Preparative Example 2

Diethyl malonate (30 gm) was added to 1-(4-cyanophenyl) guanidine (30 gm) at room temperature. A solution of sodium (17.2 gm) in ethanol (450 ml) was added to the above reaction mass. The contents were heated to reflux and maintained for 12 hours. Distilled off the solvent completely under vacuum and then added water (500 ml). The reaction mass was stirred for 30 minutes and filtered. The solid obtained was dried to obtain 40 gm of 4-(4,6-dihydroxypyrimidine-2-yl-amino) benzonitrile.

Preparation of 4-(4,6-dichloropyrimidine-2-yl-amino)benzonitrile

Preparative Example 3

Phosphoryl chloride (159 ml), N,N-dimethyl aniline (118 ml) and 4-(4,6-dihydroxypyrimidine-2-yl-amino)benzonitrile (40 gm) are added and heated to reflux. The reaction mass was maintained for 6 hours at reflux and then poured into ice water (1000 ml). The reaction mass stirred for 2 hours at room temperature and filtered. The solid obtained was dried to obtain 35 gm of 4-(4,6-dichloropyrimidine-2-yl-amino)benzonitrile.

Preparation of 4-[[6-chloro-2-[(4-cyanophenyl) amino]-4-pyrimidinyl]oxy]-3,5-dimethylbenzonitrile Example 1

4-(4,6-Dichloropyrimidine-2-yl-amino)benzonitrile (35 gm) as obtained in preparative example 3 was added to 4-hydroxy-3,5-dimethylbenzonitrile (22 gm) and then added a mixture of N-methylpyrrolidone and potassium carbonate (22 gm) at 45° C. The reaction mass was stirred for 12 hours at 45° C. and added water (1000 ml). The reaction mass was cooled to 25° C. and stirred for 2 hours at 25° C., filtered. The wet solid obtained was dissolved in acetone (140 ml) under stirring and the separated solid was filtered, and then dried at 50° C. to obtain 24 gm of 4-[[6-chloro-2-[(4-cyanophenyl)amino]-4-pyrimidinyl]oxy]-3,5-dimethylbenzonitrile.

Preparation of 4-[[6-amino-2-[(4-cyanophenyl) amino]-4-pyrimidinyl]oxy]-3,5-dimethylbenzonitrile Example 2

4-[[6-chloro-2-[(4-cyanophenyl)amino]-4-pyrimidinyl] oxy]-3,5-dimethyl-benzonitrile (24 gm) was dissolved in aqueous ammonia (240 ml) and 1,4-dioxane (274 ml) at room temperature. The contents were heated to 120° C. and maintained for 12 hours at 120° C. To the reaction mass was added water (360 ml) and the reaction mass was slowly cooled to 50 to 60° C. The reaction mass was further cooled to 0 to 5° C. and stirred for 1 hour at 0 to 5° C., filtered. The wet solid obtained was dissolved in toluene (150 ml) under stirring. The separated solid was filtered and dried at 50° C. to obtain 10 gm of 4-[[6-amino-2-[(4-cyanophenyl)amino]-4-pyrimidinyl] oxy]-3,5-dimethylbenzonitrile.

Preparation of Etravirine

Example 3

4-[[6-amino-2-[(4-cyanophenyl)amino]-4-pyrimidinyl] oxy]-3,5-dimethyl-benzonitrile (10 gm) was dissolved in dichloromethane (100 ml) at 0 to 5° C. and then added bromine solution (4.7 gm in 50 ml of dichloromethane). The reaction mass was stirred for 4 hours at 0 to 5° C. and then added water (100 ml). The pH of the reaction mass was adjusted to 9 to 10 with sodium hydroxide solution (4N, 10 ml). Sodium metabisulphite solution (0.5 gm in 2 ml of water) was added to the reaction mass and pH of the reaction mass was maintained between 7.5 to 8.5 with sodium hydroxide solution (4N, 10 ml). The separated solid was filtered and dried at 50 to 55° C. to obtain crude etravirine.

Crude etravirine obtained above was dissolved in acetone (200 ml) at 50 to 55° C. and then treated with activated charcoal (1.5 gm). The reaction mass was filtered through celite and the filtrate was distilled off acetone completely to obtain residue. The residue was cooled to 5 to 10° C. and filtered. The solid obtained was dried at 60° C. to obtain 5.2 gm of pure etravirine.

Preparation of Etravirine Crystalline Form I

Example 4

Etravirine (500 mg) as obtained example 3 was dissolved in tetrahydrofuran (5 ml) under stirring at room temperature. The insolubles were filtered. To the filtrate was added n-heptane (15 ml) and stirred for 1 hour at room temperature. The separated solid was filtered and dried under vacuum for 1 hour to obtain 460 mg of etravirine crystalline form I.

Example 5

Etravirine (2 gm) was dissolved in 1,4-dioxane (25 ml) under stirring at room temperature. The insolubles were filtered. To the filtrate was added n-heptane (60 ml) and stirred for 1 hour at room temperature. The separated solid was filtered and dried under vacuum for 1 hour to obtain 1.8 gm of etravirine crystalline form I.

Example 6

Etravirine (500 mg) was dissolved in N-methylpyrrolidone (5 ml) at room temperature. To the reaction mass was added water (10 ml) and stirred for 2 hour at room temperature, filtered. The solid obtained was dried under vacuum for 1 hour to obtain 450 mg of etravirine crystalline form I.

Example 7

Etravirine (1 gm) was dissolved in dimethylacetamide (10 ml) at room temperature. To the reaction mass was added water (18 ml) and stirred for 2 hour at room temperature, filtered. The solid obtained was dried under vacuum for 1 hour to obtain 0.85 gm of etravirine crystalline form I.

Example 8

Example 4 was repeated using methyl tert-butyl ether solvent instead of tetrahydrofuran solvent to obtain etravirine crystalline form I.

Example 9

Example 4 was repeated using methylene dichloride solvent instead of tetrahydrofuran solvent to obtain etravirine crystalline form I.

Example 10

Example 4 was repeated using ethyl acetate solvent instead of tetrahydrofuran solvent to obtain etravirine crystalline form I.

Example 11

Example 4 was repeated using methanol solvent instead of tetrahydrofuran solvent to obtain etravirine crystalline form I.

Example 12

Example 4 was repeated using dimethylformamide solvent instead of tetrahydrofuran solvent to obtain etravirine crystalline form I.

Example 13

Example 4 was repeated using dimethylsulfoxide solvent instead of tetrahydrofuran solvent to obtain etravirine crystalline form I.

Example 14

Etravirine crystalline form II (2 gm) was dissolved in tetrahydrofuran (18 ml) under stirring at room temperature. The insolubles were filtered. To the filtrate was added n-heptane (55 ml) and stirred for 1 hour at room temperature. The separated solid was filtered and dried under vacuum for 1 hour to obtain 1.8 gm of etravirine crystalline form I.

Example 15

Example 14 was repeated using etravirine crystalline form III instead of etravirine crystalline form II to obtain etravirine crystalline form I.

Preparation of Etravirine Crystalline Form II

Example 16

Etravirine (500 mg) was dissolved in a mixture of methanol (30 ml) and methylene dichloride (30 ml) at room temperature. The insolubles were filtered. The filtrate was stirred for 15 minutes and distilled off the solvent completely under vacuum. The solid obtained was dried under high vacuum for 15 minutes to obtain 460 mg of etravirine crystalline form II.

Example 17

Etravirine (2 gm) was dissolved in a mixture of methanol (110 ml) and methylene dichloride (120 ml) at room temperature. The insolubles were filtered. The filtrate was stirred for 15 minutes and distilled off the solvent completely under vacuum. The solid obtained was dried under high vacuum for 15 minutes to obtain 1.8 gm of etravirine crystalline form II.

Example 18

Example 16 was repeated using ethanol solvent instead of methanol solvent to obtain etravirine crystalline form II.

Example 19

Example 16 was repeated using etravirine crystalline form I instead of etravirine to obtain etravirine crystalline form II.

Example 20

Example 16 was repeated using etravirine crystalline form III instead of etravirine to obtain etravirine crystalline form II.

Preparation of Etravirine Crystalline Form III

Example 21

Etravirine (500 mg) was dissolved in a mixture of methanol (36 ml) and methylene dichloride (24 ml) at room temperature. The reaction mass was stirred for 12 hours at room temperature and the insolubles were filtered. The filtrate was distilled off the solvent completely under vacuum to obtain a residue. To the residue was added tert-butyl methyl ether (20 ml) and stirred for 15 minutes at room temperature. The separated solid was filtered and dried under vacuum for 10 minutes to obtain 455 mg of etravirine crystalline form III.

Example 22

Etravirine (1 mg) was dissolved in a mixture of methanol (80 ml) and methylene dichloride (48 ml) at room temperature. The reaction mass was stirred for 12 hours at room temperature and the insolubles were filtered. The filtrate was distilled off the solvent completely under vacuum to obtain a residue. To the residue was added tert-butyl methyl ether (20 ml) and stirred for 15 minutes at room temperature. The separated solid was filtered and dried under vacuum for 10 minutes to obtain 0.82 gm of etravirine crystalline form III.

Example 23

Example 21 was repeated using ethanol solvent instead of methanol solvent to obtain etravirine crystalline form III.

Example 24

Example 21 was repeated using etravirine crystalline form I instead of etravirine to obtain etravirine crystalline form III.

Example 25

Example 21 was repeated using etravirine crystalline form II instead of etravirine to obtain etravirine crystalline form III.

We claim:

1. A process for the preparation of 4-[[6-chloro-2-[(4-cyanophenyl)amino]-4-pyrimidinyl]oxy]-3,5-dimethylbenzonitrile of formula I:

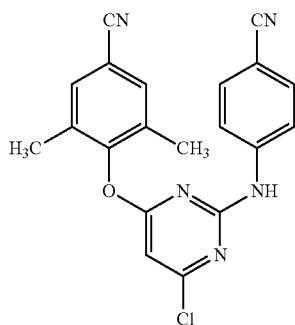

comprising reacting a 4-(4,6-dichloropyrimidine-2-yl-amino)benzonitrile of formula II:

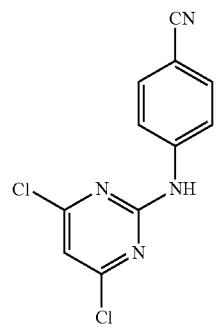

with 4-hydroxy-3,5-dimethylbenzonitrile of formula III:

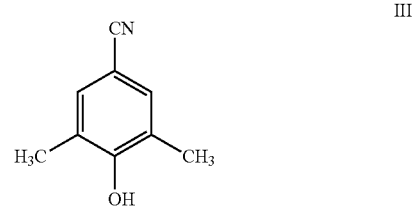

in the presence of a base to provide the compound of formula I.

2. The process according to claim 1, wherein the base used in the process is organic base or inorganic base.

3. The process according to claim 2, wherein the base is an inorganic base selected from the group consisting of alkali metal hydroxides, alkali metal carbonates and alkali metal bicarbonates.

4. The process according to claim 3, wherein the base is potassium carbonate.

5. The process according to claim 1, wherein the reaction is carried out in a solvent selected from the group consisting of N-methylpyrrolidone, dimethylformamide, dimethylacetamide, and 1,4-dioxane.

6. The process according to claim 5, wherein the solvent is N-methylpyrrolidone.

7. A process for the preparation of etravirine crystalline form I, comprising:
   a. providing a solution of etravirine in an organic solvent;
   b. adding a solvent selected from the group consisting of water and a hydrocarbon solvent to the solution obtained in step (a); and
   c. isolating etravirine crystalline from 1 the solution of step (b).

8. The process according to claim 7, wherein the organic solvent used in step (a) is a solvent or mixture of solvents selected from the group consisting of methanol, ethanol, isopropyl alcohol, ethyl acetate, methyl acetate, isopropyl acetate, tert-butyl methyl acetate, ethyl formate, acetonitrile, dimethylformamide, dimethylsulfoxide, methylene chloride, chloroform, carbontetrachloride, ethylene dichloride, tetrahydrofuran, 1,4-dioxane, tert-butyl methyl ether, diethyl ether; N-methylpyrrolidone, and dimethylacetamide.

9. The process according to claim 8, wherein the organic solvent is selected from the group consisting of ethyl acetate, methyl acetate, isopropyl acetate, tert-butyl methyl acetate, N-methylpyrrolidone and dimethylacetamide.

10. The process according to claim 9, wherein the organic solvent is selected from the group consisting of tetrahydrofuran, 1,4-dioxane, N-methylpyrrolidone and dimethylacetamide.

11. The process according to claim 7, wherein the hydrocarbon solvent used in step (b) is a solvent or mixture of solvents selected from the group consisting of cyclohexane, hexane, n-heptane, benzene, toluene and xylene.

12. The process according to claim 11, wherein the hydrocarbon solvent is n-heptane.

13. An etravirine crystalline form II which is characterized by peaks in the powder x-ray diffraction spectrum having 2θ angle positions at about 11.1, 12.2, 13.1, 13.8, 18.1, 18.4, 19.8, 21.3, 22.7, 22.9, 24.5 and 27.2±0.2 degrees.

14. The etravirine crystalline form II of claim 13, characterized by an x-ray powder diffractogram as shown in FIG. 2.

15. A process for the preparation of etravirine crystalline form II as claimed in claim 13, comprising:
   a. providing a solution of etravirine in a mixture of an alcoholic solvent and a chlorinated solvent in a ratio of 0.7:1 to 1.2:1;
   b. removing the solvent completely from the solution obtained in step (a); and
   c. drying the solid obtained in step (b) to obtain etravirine crystalline from II.

16. The process according to claim 15, wherein the alcoholic solvent used in step (a) is a solvent or mixture of solvents selected from the group consisting of methanol, ethanol and isopropyl alcohol.

17. The process according to claim 15, wherein the chlorinated solvent used in step (a) is a solvent or mixture of solvents selected from methylene chloride, chloroform, carbontetrachloride and ethylene dichloride.

18. An etravirine crystalline form III which is characterized by peaks in the powder x-ray diffraction spectrum having 2θ angle positions at about 6.0, 8.7, 9.1, 11.2, 12.1, 13.7, 18.1, 19.8, 22.9, 24.4, 25.3 and 27.3±0.2 degrees.

19. The etravirine crystalline form III of claim 18, characterized by an x-ray powder diffractogram as shown in FIG. 3.

20. A process for the preparation of etravirine crystalline form III as claimed in claim 18, comprising:
   a. stirring a solution of etravirine in a mixture of an alcoholic solvent and a chlorinated solvent in a ratio of 1.3:1 to 2:1;
   b. removing the solvent partially or completely from the solution obtained in step (a) to form a reaction mass;
   c. adding an ether solvent to the reaction mass obtained in step (b); and
   d. isolating etravirine crystalline from III from the solution in step (c).

21. The process according to claim 20, wherein the alcoholic solvent used in step (a) is a solvent or mixture of solvents selected from the group consisting of methanol, ethanol and isopropyl alcohol.

22. The process according to claim 20, wherein the chlorinated solvent used in step (a) is a solvent or mixture of solvents selected from the group consisting of methylene chloride, chloroform, carbontetrachloride and ethylene dichloride.

23. The process according to claim 20, wherein the ether solvent used in step (c) is a solvent or mixture of solvents selected from the group consisting of tetrahydrofuran, 1,4-dioxane, tert-butyl methyl ether and diethyl ether.

* * * * *